US00PP09204P

United States Patent [19]

Klemm

[11] Patent Number: Plant 9,204

[45] Date of Patent: Jul. 18, 1995

[54] GERANIUM PLANT 'KLEGOES'

[76] Inventor: Siegfried Klemm, Hanfäcker 8, D 70378 Stuttgart, Germany

[21] Appl. No.: 285,864

[22] Filed: Aug. 4, 1994

[51] Int. Cl.[6] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Arnold, White & Durkee

[57] ABSTRACT

Geranium Klegoes is a new and distinct cultivar of germanium, botanically known as *Pelargonium*×*zonale* Hybriden. It is distinguished from other geranium plants by its compact form, precocity, and rich pink flower color with a center white region.

1 Drawing Sheet

BACKGROUND OF THE NEW PLANT

Klegoes is the product of a breeding program that has the objective of developing new geranium plants with good precocity and floral richness with overall harmony of form.

Klegoes originated from the pollen parent Mareli (U.S. Plant Pat. No. 6,997), tradenamed Catania, and seed parent Romanze. Romanze was originally sold by the Dümmen Company in Rheinberg, Germany but is no longer sold and to the inventor's knowledge is no longer available.

Compared with its seed parent Romanze, the new cultivar has a better cutting production. Klegoes has color similar to Mareli's frosty light pink color. However, Mareli is a less vigorous grower and lacks the floral richness of the new cultivar. The precocity and floral richness of the new geranium plant were noticeable in contrast to these same characteristics of the parents.

The new plant was first discovered in Stuttgart in 1989 as a result of a controlled breeding program. Klegoes was the progeny of a cross between the seed parent Romanze and the pollen parent Mareli and was selected by the inventor as one flowering plant that showed unusual floral richness by comparison with either parent.

The first act of asexual reproduction of Klegoes was accomplished when vegetative cuttings were taken from the initial selection in a controlled environment in Stuttgart, Germany by the inventor or technicians working under the supervision of the inventor. Horticultural examination of selected plants demonstrated that the combination of characteristics herein disclosed for Klegoes are firmly fixed and are retained through successive generations of asexual reproduction.

Klegoes has not been observed under all possible environmental conditions. The phenotype may vary significantly with variations in environment such as temperature, light intensity, and daylength. The following observations, measurements, and comparisons describe plants grown in Stuttgart, Germany under conditions that approximate those used in commercial practice. Similar characteristics are found when the plant is grown under controlled environmental conditions in Italy and the Netherlands.

Compared with other varieties of the same species, Kelgoes has sufficient and very uniform precocity. Growth is regular, uniform, and habit is compact. Because of the uniformity no selection is necessary, making the plants quite marketable. Transportability is excellent because the plants are not shattering and long lasting. Flowers show good weather resistance with little fading in sun or heat and no evidence of rotting in rain or cold weather. The leaves are leathery and robust and also quite weather resistant.

The plants flower continuously with no break in the summer while maintaining a very attractive appearance even in hot weather. Floral richness is also extraordinarily good during hot summer weather. Good growth and flowering characteristics were observed under growing conditions in Germany, Italy, Netherlands, and Teneriffe. Good flowering characteristics were observed in cooler regions. Even richer flowering was observed in warm climates. Cutting production is very good and normal rooting is observed. Cuttings are readily transported unrooted or rooted. Flower color is very bright and thus attracts attention. Florets have an attractive appearance and fullness of shape. The umbel shape and stem length provide a harmonious and attractive appearance. The regular compact growth and posture of the umbels on usually vertical stems add to the harmonious appearance of the plant.

DESCRIPTION OF THE PHOTOGRAPH

The accompanying color photograph of Klegoes illustrates typical inflorescence and leaf characteristics of the new plant. The plant was photographed using professional photographic techniques. The view is taken against a blue background. It illustrates flower color closest to the color values in accordance with the Royal Horticultural Society Colour Chart. The background highlights the light pink color of the florets.

DESCRIPTION OF THE PLANT

The following description uses color references from the Royal Horticultural Society Colour Chart. The color values were determined under prevailing conditions natural daylight in a greenhouse environment during the month of March in Stuttgart, Germany.

The following traits have been repeatedly observed and are determined to be basic characteristics of Klegoes that in combination distinguish this geranium as a new and distinct cultivar. These characteristics include a semi-double frosty light pink flower with a white center. The plant shows some resistance to botrytis and has a vigorous upright growth habit.

Classification:

*Botanical.*—*Pelargonium*×*zonale* — Hybriden.

*Commercial.*—Klegoes, Zonale Geranium.

The Plant:

*Form.*—Bush.

*Shape.*—Round, symmetrical (as observed from above).

*Height.*—190–240 mm at maturity (typically in September in Germany).

*Growth.*—Vigorous, upright.

*Time from rooted cutting to flowering.*—Time from rooted cutting to flowering takes 95 days when cultivation is at 15° C.

*Precocity.*—Early (marketable date is April 9–14 when propagated January 6–9. This is earlier than medium varieties.

*Pinching to induce branching.*—Not required; this plant is highly self branching.

*Stem length*—140–180 mm (indoor); 130–150 mm (outdoor, summer).

*Internode length.*—10 mm.

*Leaf stem length.*—30–60 mm.

*Branching character.*—Very good.

*Number of stems per stalk.*—2–3.

*Number of stalks per plant.*—5–6.

*Foliage.*—Quantity — many, small leaves of good uniformity. Shape — round. Margin type — bicrenated. Size — leaf length averages 5.0 cm; leaf width averages 7.0–8.5 cm. Texture: Old leaves — leathery. Young leaves — smooth. Color: Upperside — 146A. Underside — 146B. Zonation — 147A becomes more conspicuous (darker) when plants are grown under conditions where night temperatures range from 8°–10° C.

*Leaf stem.*—4.0–8.0 cm in length.

Inflorescence:

*Florets.*—Number of florets — 60–70 per cluster or umbel. Size — 4.5 cm. Fullness — semi-double. Shape — cup-shape when first opened becoming more flat with maturity. Perfect — pistils and stamens present. Arrangement — imbricated.

*Petal form.*—Broad.

*Margin type.*—Entire.

*Persistence of petals.*—6 days if not pollinated.

*Texture.*—Soft.

*Appearance.*—Satiny.

*Petal size.*—2.2–2.4 cm length, 2.2–2.3 cm width.

*Color.*—Outer petal: Body — RHS 65A. Base — The attachment portion, claw and basal portions of the petals are normally white near RHS 155D, and may have dark or light veins. The white color suffuses abruptly into the predominantly light red-purple petal color. The reverse side is 65C. Inside petal: Body — 68B. Base — 70D. Reverse side — 69B. Petaloids: Number — 1–3. Size — 0.3–1.2 cm in length; 0.6–1.2 cm in width. Color — RHS 68B, or of a coloration similar to the inside petals. Flower stem (petiole): Length — 22 mm. Color — light green. Strength — medium.

*Arrangement of pedicels.*—Normal for species; as clustered flowers are open, pedicels radiate upwardly and outwardly from the apex of the peduncle with the mature flowers in the middle of the cluster.

*Discoloration after full bloom.*—None.

*Effect of hot or wet weather.*—None (none to very little).

*Persistence.*—Flower persists (at maturity, flower dries and folds down).

*Disease resistance.*—Somewhat resistent to botrytis.

*Fragrance.*—None.

*Lasting quality.*—On plant — 23 days. Cut flower — 6 days.

To determine "lasting quality", old florets are not removed and the length of time observed for long flowering clusters to maintain appearance is determined. This is measured as the number of days from the day when the first flower opens to the day when the last flower opens. This depends on the number of florets found in one cluster and with geraniums generally may vary from 20 to more than 70. The average number for the lasting quality is determined from the length of time the clusters maintain their attractive appearance.

Bud:

*Size.*—9 mm (medium).

*Depth or length.*—15 mm.

*Form.*—Thick and short pointed (pointed and ovoid).

*Rate of opening.*—Medium by comparison with typical geraniums.

*Color of petals/florets.*—When sepals first divide — very light pink. When petals begin to unfurl — light pink with pink stripes.

Sepals:

*Shape.*—Long and pointed.

*Number.*—5 (when flowers open, sepals reflex).

*Color.*—Inside — 144B. Outside — 144B.

*Simultaneously appearing buds and flower clusters.*—Young marketable plants show four buds and two clusters.

*Mature plants (up until the middle of May).*—Eight to nine matured clusters will be picked off between the date when plants are marketable and the middle of May when the plants are placed outdoors.

*Mature plants under outside conditions.*—(May to September) 60–105 depending on weather conditions. More flowers are observed during hot weather. Pinching of spent clusters is not required to maintain active flowering. Picking of matured clusters produces a more aesthetic appearance.

Reproductive organs:

*Stamens.*—Number — 6 arranged around the ovaries. Anthers: Size — 2.1 mm. Color — dark pink. Filaments (threads): Length — 7 mm. Color — white.

*Pollen.*—Color — orange.

*Pistils.*—Number — 1 with 5 with a five-segmented stigma.

*Styles.*—Length — 10 mm. Color — light pink and green.

*Stigmas.*—Color — dark pink.

Fruit:

*Fertile.*—Yes.

*Color.*—Green becoming sand colored after maturity.

*Length of seed.*—3–4.5 mm.

*Color of seed.*—Brown.

What is claimed is:

1. A new and distinct geranium cultivar, substantially as herein described as shown, characterized by its frosty light pink color and fade resistance to sun and heat.

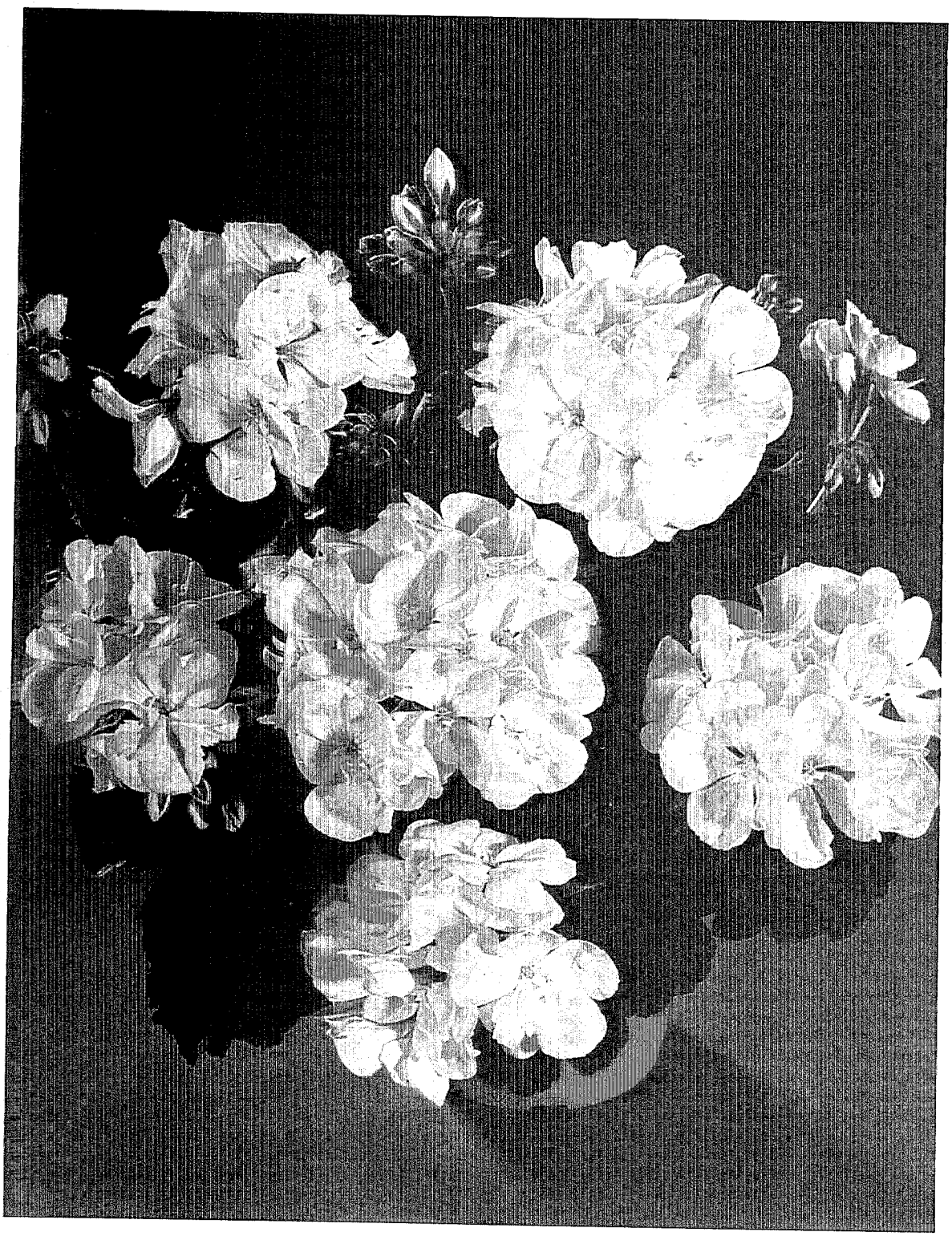

* * * * *